(12) United States Patent
Sutheerawattananonda et al.

(10) Patent No.: US 9,018,422 B2
(45) Date of Patent: Apr. 28, 2015

(54) METHOD FOR EXTRACTING SILK EXTRACT CONTAINING LUTEIN

(76) Inventors: Manote Sutheerawattananonda, Nakorn Ratchasima (TH); Potchanee Kaewkumsan, Nakorn Ratchasima (TH); Nanteetip Limpeanchob, Phitsanulok (TH); Duangkamol Kanthalert, Phitsanulok (TH)

( * ) Notice: Subject to any disclaimer, the term of this patent is extended or adjusted under 35 U.S.C. 154(b) by 151 days.

(21) Appl. No.: 13/977,179

(22) PCT Filed: Dec. 30, 2010

(86) PCT No.: PCT/TH2010/000048
§ 371 (c)(1),
(2), (4) Date: Aug. 28, 2013

(87) PCT Pub. No.: WO2012/091683
PCT Pub. Date: Jul. 5, 2012

(65) Prior Publication Data
US 2013/0331615 A1    Dec. 12, 2013

(51) Int. Cl.
C07C 29/86    (2006.01)
C07C 403/24    (2006.01)
A61K 31/047    (2006.01)
C07K 14/435    (2006.01)
A61L 27/22    (2006.01)

(52) U.S. Cl.
CPC ............ *C07C 29/86* (2013.01); *C07K 14/43586* (2013.01); *A61L 27/225* (2013.01); *C07C 403/24* (2013.01); *C07C 2101/16* (2013.01); *A61K 31/047* (2013.01)

(58) Field of Classification Search
None
See application file for complete search history.

(56) References Cited

U.S. PATENT DOCUMENTS

| 5,382,714 A | 1/1995 | Khachik |
| 6,504,067 B1 | 1/2003 | Montoya-Olvera |
| 7,173,145 B2 | 2/2007 | Khachik |
| 2009/0274660 A1 | 11/2009 | Girsh |

FOREIGN PATENT DOCUMENTS

| EP | 2096177 A2 | 9/2009 |
| WO | WO 03/037833 A1 | 5/2003 |

OTHER PUBLICATIONS

Prommuak, C. et al. Separation and Purification Technology, 2008, 62, 444-448.*
Jiang, P. et al. Materials Science 2006, 60, 919-925.*
Pretreatment of Silk—Degumming Process, Copyright 2006-2013, p. 1.*

* cited by examiner

*Primary Examiner* — Fereydoun G Sajjadi
*Assistant Examiner* — Medhanit Bahta
(74) *Attorney, Agent, or Firm* — Ming Chow; Sinorica, LLC

(57) ABSTRACT

A method for obtaining silk extract containing lutein according to an embodiment of the invention is described. The lutein extraction method uses a three solvent system for extracting bioactive lutein from silk fibers. The extracted lutein has more than 95% purity in all-E isomer with biological activity being 5 times more effective on lipid peroxidation in retina cells and twice immune stimulation in mice when compared with commercially available lutein.

17 Claims, 13 Drawing Sheets

| Sample | λmax (nm) | | | %III/I[c] | Lutein content[a] | | | |
|---|---|---|---|---|---|---|---|---|
| | I[b] | II | III | | wet basis | | dry basis | |
| | | | | | (mg/100g) | (%by wt.) | (mg/100g) | (%by wt.) |
| S1 | (420) | 443 | 469 | 15[a] | 20.338[c] ± 1.516 | 0.0203[c] ± 0.0015 | 22.528[c] ± 1.527 | 0.0225[c] ± 0.0017 |
| S2 | (420) | 443 | 469 | 11[d] | 23.787[ab] ± 2.592 | 0.0238[ab] ± 0.0026 | 26.348[ab] ± 2.611 | 0.0264[ab] ± 0.0029 |
| S3 | (421) | 442 | 469 | 13[c] | 22.751[b] ± 1.792 | 0.0228[b] ± 0.0018 | 25.200[b] ± 1.805 | 0.0252[b] ± 0.0020 |
| S4 | (420) | 442 | 469 | 13[bc] | 12.253[e] ± 0.899 | 0.0123[e] ± 0.0009 | 13.572[e] ± 0.905 | 0.0136[e] ± 0.0010 |
| S5 | (421) | 443 | 469 | 14[ab] | 15.176[d] ± 0.939 | 0.0152[d] ± 0.0009 | 16.810[d] ± 0.946 | 0.0168[d] ± 0.0010 |
| S6 | (419) | 442 | 467 | 12[c] | 5.114[f] ± 0.126 | 0.0051[f] ± 0.0001 | 5.664[f] ± 0.127 | 0.0057[f] ± 0.0001 |
| S7 | (420) | 443 | 469 | 13[c] | 24.316[a] ± 0.625 | 0.0243[a] ± 0.0006 | 26.934[a] ± 0.630 | 0.0269[a] ± 0.0007 |

[a] Average of triplicate determinations ± standard deviation. [b] Values in parentheses represent shoulder. [c] %III/II represents the spectral fine structure, the shape of the spectrum. Yellow silk cocoons were degummed at 121°C for 15 min and then extracted with (S1) hexane/ethanol (3:4, v/v), (S2) hexane/acetone (5:3, v/v), (S3) hexane/acetone/ethanol (3:1:2, v/v/v), (S4) hexane/ethyl acetate (1:1, v/v), (S5) ethyl acetate (100%), (S6) hexane (100%), and (S7) hexane/ethanol/ethyl acetate (3:2:1, v/v/v). Different letters on the same column indicate significant differences ($p \leq 0.05$).

FIG. 2

| Temp. (C) | Time (min) | Degumming solution[a] | | | | | | Lutein content | | | | Degummed cocoons[a] | |
|---|---|---|---|---|---|---|---|---|---|---|---|---|---|
| | | Total solid (%by wt.) | | Protein content | | | | (mg/100g) | (%dry basis) | | | Lutein content | |
| | | degumming solution | cocoons | (g/100ml) | (%dry basis) | (mg/100ml) | (%dry basis) | | cocoons wt. | total solid | | (mg/100g) | (%dry basis) |
| 85 | 30 | 0.11$^j$ ± 0.01 | 3.82$^j$ ± 0.17 | 0.094$^a$ ± 0.015 | 3.468$^e$ ± 0.550 | 0.0006$^j$ ± 0.0001 | 0.113$^j$ ± 0.013 | 0.00011$^j$ ± 0.00001 | 0.0006$^j$ ± 0.0001 | 0.00053$^j$ ± 0.00002 | | 46.877$^a$ ± 1.355 | 0.0516$^a$ ± 0.0015 |
| | 60 | 0.13$^{ij}$ ± 0.01 | 4.23$^{ij}$ ± 0.29 | 0.133$^b$ ± 0.023 | 4.923$^d$ ± 0.861 | 0.0002$^j$ ± 0.0001 | 0.041$^j$ ± 0.017 | 0.00004$^j$ ± 0.00002 | 0.0002$^j$ ± 0.0001 | 0.00016$^f$ ± 0.00002 | | 45.269$^b$ ± 1.004 | 0.0498$^b$ ± 0.0011 |
| | 90 | 0.12$^j$ ± 0.00 | 3.99$^j$ ± 0.13 | 0.071$^a$ ± 0.028 | 2.622$^e$ ± 1.047 | 0.0002$^j$ ± 0.0001 | 0.037$^j$ ± 0.013 | 0.00004$^j$ ± 0.00001 | 0.0002$^j$ ± 0.0001 | 0.00017$^f$ ± 0.00001 | | 44.188$^c$ ± 1.410 | 0.0486$^c$ ± 0.0016 |
| | 120 | 0.13$^j$ ± 0.01 | 4.28$^j$ ± 0.26 | 0.118$^e$ ± 0.017 | 4.367$^e$ ± 0.612 | 0.0002$^j$ ± 0.0001 | 0.037$^j$ ± 0.011 | 0.00004$^j$ ± 0.00001 | 0.0002$^j$ ± 0.0001 | 0.00015$^f$ ± 0.00001 | | 41.859$^d$ ± 1.188 | 0.0460$^d$ ± 0.0013 |
| 105 | 15 | 0.41$^h$ ± 0.02 | 13.80$^h$ ± 0.68 | 0.418$^d$ ± 0.070 | 15.442$^d$ ± 2.590 | 0.0403$^e$ ± 0.0099 | 9.110$^b$ ± 0.737 | 0.00911$^e$ ± 0.00074 | 0.0403$^e$ ± 0.0099 | 0.00959$^c$ ± 0.00266 | | 29.297$^e$ ± 2.450 | 0.0322$^e$ ± 0.0027 |
| | 30 | 0.54$^g$ ± 0.02 | 17.97$^g$ ± 0.54 | 0.542$^c$ ± 0.049 | 20.000$^c$ ± 1.800 | 0.0780$^d$ ± 0.0050 | 14.372$^a$ ± 0.893 | 0.01437$^b$ ± 0.00089 | 0.0780$^d$ ± 0.0050 | 0.01467$^b$ ± 0.00122 | | 26.979$^f$ ± 0.641 | 0.0297$^f$ ± 0.0007 |
| | 60 | 0.55$^f$ ± 0.01 | 18.48$^f$ ± 0.48 | 0.808$^b$ ± 0.142 | 29.851$^b$ ± 5.249 | 0.1010$^c$ ± 0.0064 | 18.593$^c$ ± 1.201 | 0.01859$^a$ ± 0.00120 | 0.1010$^c$ ± 0.0064 | 0.01808$^a$ ± 0.00122 | | 20.198$^j$ ± 0.372 | 0.0222$^j$ ± 0.0004 |
| | 90 | 0.64$^e$ ± 0.02 | 21.30$^e$ ± 0.61 | 1.004$^a$ ± 0.084 | 37.054$^a$ ± 3.100 | 0.1157$^a$ ± 0.0029 | 21.328$^a$ ± 0.548 | 0.02133$^a$ ± 0.00055 | 0.1157$^a$ ± 0.0029 | 0.01812$^a$ ± 0.00051 | | 18.551$^j$ ± 0.739 | 0.0204$^j$ ± 0.0008 |
| | 120 | 0.69$^d$ ± 0.02 | 22.85$^d$ ± 0.58 | 0.996$^a$ ± 0.062 | 36.786$^a$ ± 2.272 | 0.1072$^b$ ± 0.0028 | 19.748$^b$ ± 0.571 | 0.01975$^b$ ± 0.00057 | 0.1072$^b$ ± 0.0028 | 0.01572$^b$ ± 0.00051 | | 18.649$^j$ ± 0.887 | 0.0205$^j$ ± 0.0010 |
| 121 | 15 | 0.71$^c$ ± 0.01 | 23.58$^c$ ± 0.44 | 0.803$^b$ ± 0.075 | 29.651$^b$ ± 2.780 | 0.0524$^a$ ± 0.0020 | 9.652$^c$ ± 0.360 | 0.00965$^c$ ± 0.00036 | 0.0524$^a$ ± 0.0020 | 0.00737$^d$ ± 0.00028 | | 25.633$^g$ ± 0.550 | 0.0282$^g$ ± 0.0006 |
| | 30 | 0.74$^b$ ± 0.02 | 24.51$^b$ ± 0.51 | 0.837$^b$ ± 0.099 | 30.891$^b$ ± 3.656 | 0.0515$^e$ ± 0.0040 | 9.471$^a$ ± 0.729 | 0.00947$^c$ ± 0.00073 | 0.0515$^e$ ± 0.0040 | 0.00706$^d$ ± 0.00012 | | 25.396$^g$ ± 0.825 | 0.0279$^g$ ± 0.0009 |
| | 60 | 0.75$^a$ ± 0.01 | 24.90$^a$ ± 0.39 | 0.997$^a$ ± 0.083 | 36.800$^a$ ± 3.077 | 0.0460$^f$ ± 0.0012 | 8.466$^f$ ± 0.216 | 0.00847$^f$ ± 0.00022 | 0.0460$^f$ ± 0.0012 | 0.00616$^d$ ± 0.00014 | | 25.021$^g$ ± 0.559 | 0.0275$^g$ ± 0.0006 |
| | 90 | 0.75$^a$ ± 0.02 | 25.11$^a$ ± 0.83 | 0.979$^a$ ± 0.079 | 36.145$^a$ ± 2.935 | 0.0307$^g$ ± 0.0077 | 5.650$^g$ ± 1.421 | 0.00565$^g$ ± 0.00142 | 0.0307$^g$ ± 0.0077 | 0.00409$^e$ ± 0.00117 | | 23.457$^h$ ± 1.066 | 0.0258$^h$ ± 0.0012 |
| | 120 | 0.76$^a$ ± 0.02 | 25.17$^a$ ± 0.78 | 0.959$^a$ ± 0.106 | 35.405$^a$ ± 3.919 | 0.0266$^h$ ± 0.0034 | 4.878$^h$ ± 0.612 | 0.00488$^h$ ± 0.00061 | 0.0266$^h$ ± 0.0034 | 0.00353$^e$ ± 0.00050 | | 22.833$^h$ ± 0.296 | 0.0251$^h$ ± 0.0003 |
| RT[b] | 6 | - | - | - | - | - | - | - | - | - | | 0.220$^i$ ± 0.026 | 0.00022$^i$ ± 0.00003 |
| | 6 | - | - | - | - | - | - | - | - | - | | 0.220$^i$ ± 0.041 | 0.00022$^i$ ± 0.00004 |
| | 48 | - | - | - | - | - | - | - | - | - | | 0.227$^i$ ± 0.030 | 0.00023$^i$ ± 0.00003 |

[a] Average of triplicate determinations ± standard deviation. [b] Extraction of pigments from raw silk cocoons at room temperature. Different letters on the same column indicate significant differences ($p \leq 0.05$).

FIG. 3

| Temp. | Time | Total lutein content [a] | | Retention of lutein [c] | | | L/S Ratio [b] (mg/kg) | |
|---|---|---|---|---|---|---|---|---|
| | | (mg/100g) | (% wt.) | (%$_{tc}$) | (%$_{Tc}$) | (%$_{Total}$) | TP | TS |
| (°C) | (min) | | | | | | | |
| 85 | 30 | 46.990[a] ± 1.354 | 0.052[a] ± 0.001 | 100.00 | 100.00 | 100.00 | 0.33 | 0.30 |
| | 60 | 45.310[b] ± 1.014 | 0.050[b] ± 0.001 | 96.57 | 96.57 | 96.42 | 0.08 | 0.10 |
| | 90 | 44.225[b] ± 1.414 | 0.049[b] ± 0.002 | 94.26 | 94.26 | 94.12 | 0.14 | 0.09 |
| | 120 | 41.896[c] ± 1.192 | 0.046[c] ± 0.001 | 89.30 | 89.30 | 89.16 | 0.08 | 0.09 |
| 105 | 15 | 38.407[e] ± 2.738 | 0.041[e] ± 0.003 | 100.00 | 62.50 | 81.73 | 5.90 | 6.60 |
| | 30 | 41.351[c] ± 0.649 | 0.044[d] ± 0.001 | 92.09 | 57.55 | 88.00 | 7.19 | 8.00 |
| | 60 | 38.791[de] ± 1.165 | 0.041[e] ± 0.001 | 68.94 | 43.09 | 82.55 | 6.23 | 10.06 |
| | 90 | 39.880[d] ± 0.745 | 0.042[e] ± 0.001 | 63.32 | 39.57 | 84.87 | 5.76 | 10.01 |
| | 120 | 38.397[e] ± 0.584 | 0.040[e] ± 0.001 | 63.66 | 39.78 | 81.71 | 5.37 | 8.64 |
| 121 | 15 | 35.285[f] ± 0.824 | 0.038[f] ± 0.001 | 100.00 | 54.68 | 75.09 | 3.26 | 4.09 |
| | 30 | 34.867[f] ± 0.943 | 0.037[fg] ± 0.001 | 99.07 | 54.18 | 74.20 | 3.07 | 3.86 |
| | 60 | 33.487[g] ± 0.568 | 0.036[g] ± 0.001 | 97.61 | 53.38 | 71.26 | 2.30 | 3.40 |
| | 90 | 29.106[h] ± 1.003 | 0.031[h] ± 0.001 | 91.51 | 50.04 | 61.94 | 1.56 | 2.25 |
| | 120 | 27.711[i] ± 0.784 | 0.030[i] ± 0.001 | 89.08 | 48.71 | 58.97 | 1.38 | 1.94 |

[a] Total lutein content including in the degumming solution and the degummed cocoons were averaged from triplicate determinations ± standard deviation, in dry basis. [b] Values were calculated from the ration of lutein to total protein contents (TP) and total solids (TS) in 100 ml of the degumming solutions. [c] The amount of lutein extracting from the degummed cocoons represent in %remaining, compared to that of the shortest heating time of each temperature (%$_{tc}$), and the lowest temperature and time (%$_{Tc}$); total lutein content in yellow silk cocoons (%$_{Total}$) represents in %remaining comparing to that of the lowest temperature and time. Different letters on the same column indicate significant differences ($p \leq 0.05$).

FIG. 4

| Sample[b] | λmax (nm) | | %III/II | Lutein content | | | | |
|---|---|---|---|---|---|---|---|---|
| | peak II | peak III | | (mg/100g) | | | (%) | |
| | | | | wet wt. | dry wt. | | wet wt. | dry wt. |
| P1 | 445 | 473 | 41 | 46.559 ± 0.420 | 51.572 ± 1.338 | | 0.04656 ± 0.00042 | 0.05157 ± 0.00047 |
| P2 | 446 | 470 | 1 | 0.051 ± 0.006 | 0.057 ± 0.006 | | 0.00005 ± 0.00001 | 0.00006 ± 0.00001 |
| Total[c] | | | | 46.610 ± 0.426 | 51.628 ± 1.345 | | 0.04661 ± 0.00043 | 0.05163 ± 0.00047 |

[a] Average of triplicate determinations ± standard deviation. [b] Yellow cocoons in both parts of degummed cocoons (P1) and degumming solution (P2). [c] Total lutein content in yellow cocoons.

FIG. 5

| Source | Distribution of major carotenoids (mole%)[a] | | | | | | | Lutein composition[d] | | References |
|---|---|---|---|---|---|---|---|---|---|---|
| | Lutein/zeaxanthine | Cryptoxanthins | Lycopenes | α-Carotene | β-Carotene | Neoxanthins/violaxanthins | | mg/100g fresh wt. | mg/100g dry wt. | |
| Animal products: | | | | | | | | | | |
| Yellow silk cocoons (Bombyx mori) | 97 | - | - | - | 0 | 0 | - | 46.61 | 51.628 | - |
| Egg york | 89 | 84 | 4 | 0 | 0 | 0 | 8 | 3.766[11]-0.723 | - | (9), (11) |
| Fruits/vegetables: | | | | | | | | | | |
| Kale, raw | - | 54 | - | - | - | - | - | 39.550[1] | - | (1), (3), (10) |
| "Winterbor" kale | - | - | - | - | - | - | - | 15.10-6.90 | 71-112 | (2) |
| Squash, pepper peel | - | - | - | - | - | - | - | 30.180 | - | (3) |
| Squash, pepper fresl | - | - | - | - | - | - | - | 0.870 | - | (3) |
| Spinach | 47 | 47 | 19 | 4 | 0 | 16 | 14 | 11.940[1]-3.740 | 133.7[1]-34.9 | (1), (3-6) |
| Leaf lettuce | 15 | 15 | 38 | 0 | 16 | 0 | 30 | 2.635 | - | (1) |
| Broccoli | 22 | 22 | 49 | 0 | 0 | 27 | 3 | 2.445[1]-1.553 | - | (1), (10) |
| Summer squash | 52 | 47 | 24 | 0 | 0 | 5 | 19 | 2.125 | - | (1) |
| Brussel sprouts | 29 | 27 | 39 | 0 | 0 | 11 | 20 | 1.590 | - | (1) |
| Peas (green) | 41 | 41 | 21 | 0 | 0 | 5 | 33 | 1.350 | - | (1) |
| Corn | 86 | 60 | 5 | 0 | 0 | 0 | 9 | 0.884[1]-0.199 | 2.07[6] | (1), (5-6) |
| Green beans | 0 | 0 | 28 | 0 | 0 | 0 | 72 | 0.640[1]-0.453 | - | (1), (10) |
| Potato, fresh | - | - | - | - | - | - | - | 0.410-0.250 | - | (3) |
| Carrots, baby | - | - | - | - | - | - | - | 0.358 | - | (1) |
| Carrot | 2 | 2 | 0 | 0 | 43 | 55 | 0 | 0.298 | - | (5) |
| Cabbage | - | - | - | - | - | - | - | 0.310 | - | (1) |
| Oranges | 22 | 7 | 12 | 11 | 8 | 11 | 36 | 0.187 | - | (1), (10) |
| Papaya | - | - | - | - | - | - | - | 0.075[1]-0.044 | - | (10) |
| Peaches | 13 | 5 | 8 | 0 | 10 | 50 | 20 | 0.04 | - | (1) |
| Winter squash | - | - | - | - | - | - | - | 0.038 | - | (10) |
| Mango | 18 | 2 | 4 | 6 | 0 | 20 | 52 | 0.020 | - | (10) |
| Grapefruit, red | - | - | - | - | - | - | - | 0.013 | - | (1) |
| Tomatoes | 6 | 6 | 0 | 82 | 0 | 12 | 0 | 0.130[1]-0.050 | - | (1), (5) |
| Pumpkin | 49 | 49 | 0 | 0 | 0 | 21 | 30 | - | - | - |
| Flowers: | | | | | | | | | | |
| Marigold petals[b] | - | - | - | - | - | - | - | 161-611 | - | (7) |
| Marigold petals[c] | - | - | - | - | - | - | - | 16.77-569.90 | - | (8) |
| Marigold calyces[c] | - | - | - | - | - | - | - | 0.38-18.60 | - | (8) |

[a] The data from Sommerburg et al. (1998). [b] Lutein diesters in Chinese marigold flowers (T. erecta). [c] Lutein and lutein esters from marigold flowers, Tagetes patula and T. erecta. [d] Literature values refer to: (1), U.S. Department of Agriculture (1998); (2), Lefsrud et al. (2007); (3), Tsao and Yang (2006); (4), Liu, Perera and Suresh (2007); (5), Konings and Roomans (1997); (6), Aman et al. (2005); (7), Li et al. (2007); (8), Piccaglia, Marotti and Grandi (1998); (9), Handelman et al. (1999); (10), Humphries and Khachik (2003); and (11), Schlatterer and Breithaupt (2006).

FIG. 6

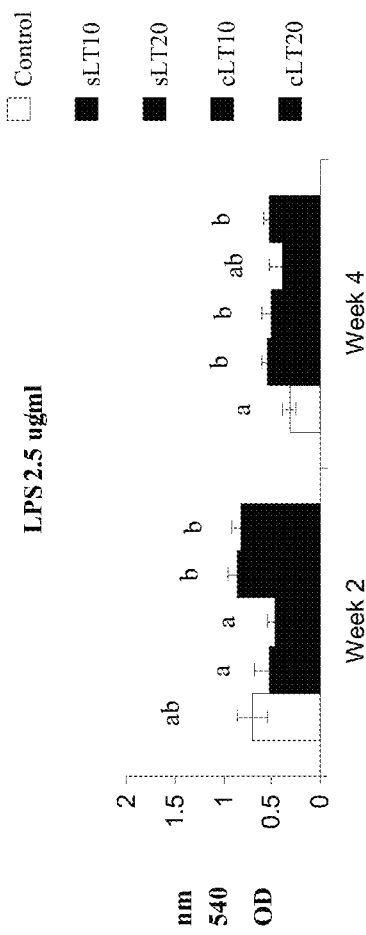
FIG. 11

METHOD FOR EXTRACTING SILK EXTRACT CONTAINING LUTEIN

FIELD OF INVENTION

The present invention relates generally to a method for extracting lutein from silk fibers. Specifically, the invention relates to a method for extracting silk extract containing lutein.

BACKGROUND

Lutein, one of xanthophylls in the family of carotenoids with non-pro-vitamin A activity, is a fat-soluble yellowish pigment found mostly in higher order of plants, algae and photosynthetic bacteria. Lutein and other carotenoids cannot be biosynthesized by animals or insects. Their presence in animals is attributed to ingestion via food and accumulation in certain tissues. Lutein and its isomer, zeaxanthin, have been identified as the only carotenoids present in specific eye tissues, specifically the macular fovea, a small area of the retina responsible for central vision and high visual acuity. In humans and in plants, lutein is believed to function as a filter of high energy blue light and is an antioxidant that quenches and scavenges photo induced reactive oxygen species (ROS) which are highly reactive and can damage DNA and lipids. Studies have shown that sufficient daily intake of lutein can greatly lead towards reducing the risk of eye diseases such as aged-related macular degradation (AMD), the leading cause of blindness among the elderly, and cataracts. Besides its bioavailability as potent antioxidant, recent studies suggest that xanthophylls, especially lutein, can be directly link to prevention of certain-types of cancer. Presence of lutein in skin and oral consumption may also serve to protect skin from UV-induced damage and may reduce the risk of cardiovascular.

Although lutein can be found in human diets with most abundantly in dark, leafy green such as spinach and kale, and foods with yellow color, such as corn and egg yolk, the average daily intake of lutein is insufficient to reduce the risk of eye diseases as well as other related symptoms. Moreover, humans can carry out only limited metabolic transformations of carotenoids, suggesting that the sufficient consumption of specific dietary carotenoids are certainly needed.

Yellow silk cocoon is one of some cocoons from many varieties of the silkworm, *Bombyx. mori*. The pigments in yellow or golden-yellow cocoons are derived from carotenoids, whereas the cocoons in others color such as yellowish green and green sasa are from flavonoids. These pigments are absorbed from mulberry leaves. They are then transferred from a midgut to silk gland via the hemolymp, and eventually accumulated in the layers of the cocoon sericin. It is emphasized that among these carotenoids, xanthophylls, principally lutein, have been indicated in previous study as predominant carotenoids in the yellow cocoons. For silk textiles, pigments partially removed from the silk cocoons do not go on to be used for other applications. Moreover, silk protein like sericin, the second main constituent of silk fibers at 20-30% of the total cocoon weight, is also mostly removed from the cocoon during degumming process. Wastewater from such process contains both lutein and sericin and is hardly treated by common wastewater management system. However, the unique functional properties of both lutein and sericin be used in food and cosmetic products as valuable natural ingredients. Consequently, isolation and extraction as well as characterization of silkworm, *B. mori*, in a form of lutein-binding protein, have been investigated.

Xanthophylls and carotene are lipid-soluble molecules that follow the absorption pathway of dietary fat. The absorption involves several steps starting from breakdown of food matrix to release of carotenoids into the lumen of the gastrointestinal tract through their incorporation into lymphatic lipoproteins. The efficient digestion and absorption of dietary fat, as well as the presence of bile salt micelles, is essential for carotenoid absorption. The study of competition among carotenoids and other dietary components for absorption, transport, and uptake by tissues well documented but requires further research. From limited data, it seems that the more polar carotenoids, xanthophylls, may be absorbed more efficiently than are carotenes, hydrocarbon carotenoids. Therefore, xanthophylls, particularly lutein and its metabolic products are well solubilized and are incorporated into surface of lipoproteins such as chylomicrons, LDL and HDL. These may enhance the transportation of lutein via blood circulating system and then accumulated in specific tissues, whereas 80-85% of hydrocarbon carotenoids preferably accumulate in the adipose tissues. In human serum, only six major carotenoids, particularly lutein and lycopene, have an estimated half life for 11-14 days. Take up of carotenoids differ for different tissues with lutein and zeaxanthin specifically accumulating in the macula region of the eye and strong associating with the decrease of AMD risk.

Lutein from Marigold flowers is an important source of lutein available in the market. It is composed of 94-97% lutein esters and 3-6% zeaxanthin. After consumption, the lutein esters need to be acid hydrolyzed into free lutein in the stomach before being absorbed into the blood serum. As several studies have indicated, only specific form of lutein can get into the blood serum and accumulate in certain organ tissues, especially the macula fovea. Lutein in the form that can be readily absorbed into the blood stream has higher bioactivity and bioavailability. Acid condition has been found to have an effect on lutein isomer transformation from E to Z form. Moreover, only lutein binding protein is found in the macula fovea, whereas lutein esters are dectected in skin and fat tissues.

Typical methods exist for isolating and purifying lutein from different plants such as marigold flowers, marigold meal, algae, red peppers, and other plant materials. Lutein isolated from these materials is in the form of an ester. The isolation processes used are complicated and involved with halogenated organic solvents. Additionally, plants and flowers used may contain a high level of herbicide and pesticide residue.

U.S. Pat. No. 5,382,714 describes a process for isolation, purification, and recrystallization of lutein from saponified marigold oleoresin. The starting material, saponified marigold oleoresin, also known as kemin yellow oil, is available commercially. After lutein isolation, the concentration of lutein crystal is around 70%. The lutein crystal is recrystallized in a mixture of dichloromethane and hexane to achieve a lutein purity level of more than 97%. The use of halogenated organic compounds in food industry is under strict regulation many territories.

PCT patent application no. WO03037833 A1 describes a method for extraction lutein from marigold meal using supercritical fluid extraction.

U.S. Pat. No. 7,173,145 B2 describes a process for extracting and purifying lutein, zeaxanthin, and rare carotenoids from marigold flowers and plants. Use of a mixture containing tetrahydrofuran and methanol was disclosed. The disadvantages of this method are the creation of a high caustic condition and the toxicity of methanol during extraction.

SUMMARY

An embodiment of the present invention described herein takes advantages of natural selected sources of lutein binding protein from silk materials. Solvents commonly allowed in food and pharmaceutical industry such as hexane, ethyl alcohol, and ethyl acetate are used. Extraction can conveniently operate at ambient condition or at high temperature and pressure. To make the process environmental friendly and economically, the solvents are evaporated and recycled for multiple uses. Subsequently, lutein purified with this present invention is in an E form with purity level of greater than 95% and has high bioactivity and bioavailability in both retina cells and mice.

In accordance with a first aspect of the invention, there is disclosed a method for lutein extraction comprising contacting silk fibres with a plurality of solvents to obtain a first solution. The plurality of solvents comprises hexane, ethyl alcohol and ethyl acetate. The method further comprises partitioning the first solution into non-aqueous phase and an aqueous phase, drying the non-aqueous phase to obtain dried residue, dissolving the dried residue with one or more of the plurality of solvents to obtain a second solution, and filtering the second solution to obtain lutein extract therefrom.

In accordance with a second aspect of the invention, there is disclosed a method for lutein extraction comprising degumming the silk cocoon to obtain silk fibres, and contacting the silk fibres with one or more solvents to obtain a first solution. The one or more solvents comprise hexane, ethyl alcohol and ethyl acetate. The method further comprises partitioning the first solution into non-aqueous phase and an aqueous phase, drying the non-aqueous phase to obtain dried residue, dissolving the dried residue with hexane and ethyl acetate to obtain a second solution, and filtering the second solution to obtain lutein extract therefrom.

In accordance with a third aspect of the invention, there is disclosed a method for lutein extraction comprising contacting silk fibres with one or more solvents to obtain a first solution. The one or more solvents comprise hexane, ethyl alcohol and ethyl acetate. The method further comprises partitioning the first solution into non-aqueous phase and an aqueous phase, drying the non-aqueous phase to obtain dried residue, dissolving the dried residue with the one or more solvents to obtain a second solution, and filtering the second solution to obtain lutein extract therefrom.

BRIEF DESCRIPTION OF THE DRAWINGS

FIG. 2 is a table showing concentration and spectral fine structure of lutein in yellow silk cocoons after extraction with various solvent systems including with a lutein extraction method according to an embodiment of the invention;

FIG. 3 is a table showing extraction efficiency of degumming process used in the lutein extraction method;

FIG. 4 shows a table tabulating influence of thermal treatment on lutein content in the degummed cocoons, lutein to sericin (L/S) ratio in the degumming solutions, and total lutein contents;

FIG. 5 shows a table of amount of lutein found in yellow silk (*Bombyx mori*) cocoons and its spectral characteristics;

FIG. 6 is a table showing composition of lutein in different sources;

FIG. 11 shows the effects of Lutein from yellow cocoon to LPS-induced lymphocyte proliferation compared with commercial lutein with LPS=2.5 ug/ml for Graph A and LPS=5 ug/ml for Graph B (values are expressed as means±SD, means with different superscripts when compared among treatment within a sampling period are significantly different: $P<0.05$; sLT10, sLT20; silk lutein dose 10, 20 mg/kg BW/day, cLT10, cLT20; commercial lutein dose 10, 20 mg/kg BW/day).

DETAILED DESCRIPTION

Figure 1:
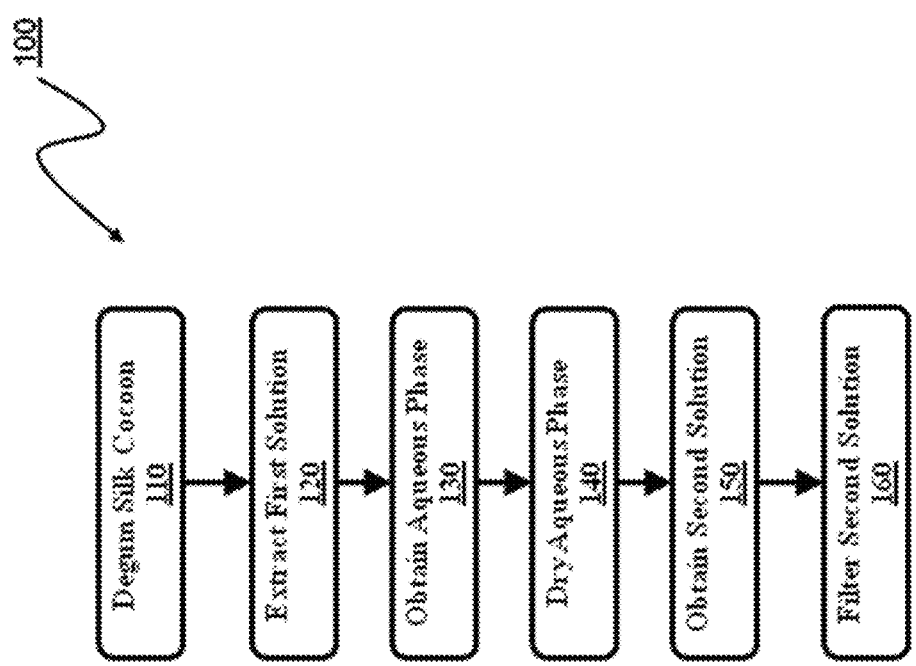
FIG. 1 shows a process flow diagram of a lutein extraction method according to an embodiment of the invention.
Figure 7:
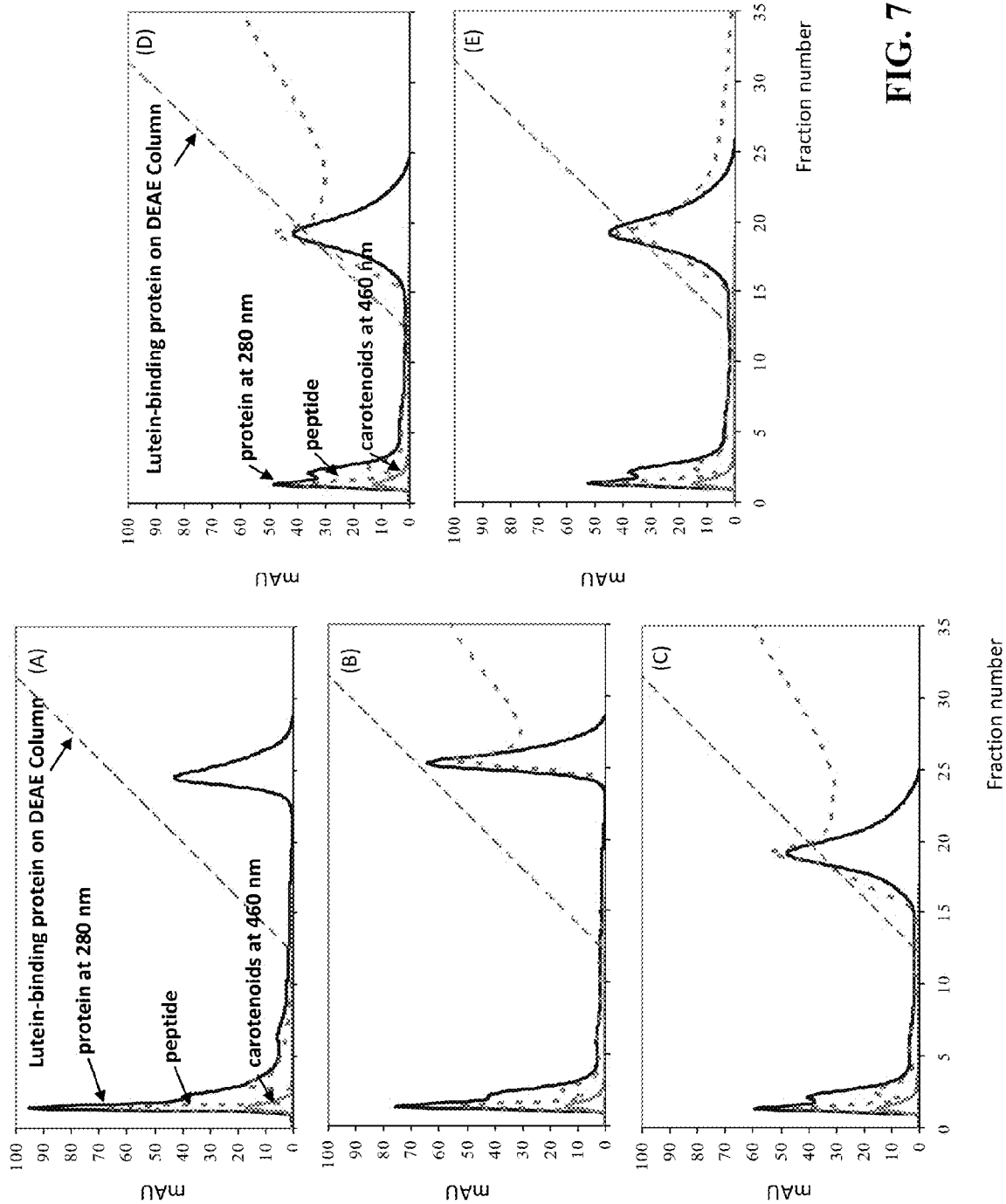
FIG. 7 shows elution profiles of the lutein-binding protein on a DEAE column where the protein obtained from degumming process at 121° C. for 15 (A), 30 (B), 60 (C), 90 (D), and 120 (E) mM were loaded onto a DEAE and eluted in a 1 M NaCl gradient in 10 mM BisTris-HCl, pH 7.0. Fractions were monitored for protein at 280 nm, carotenoids at 460 nm, and peptides.
Figure 8:
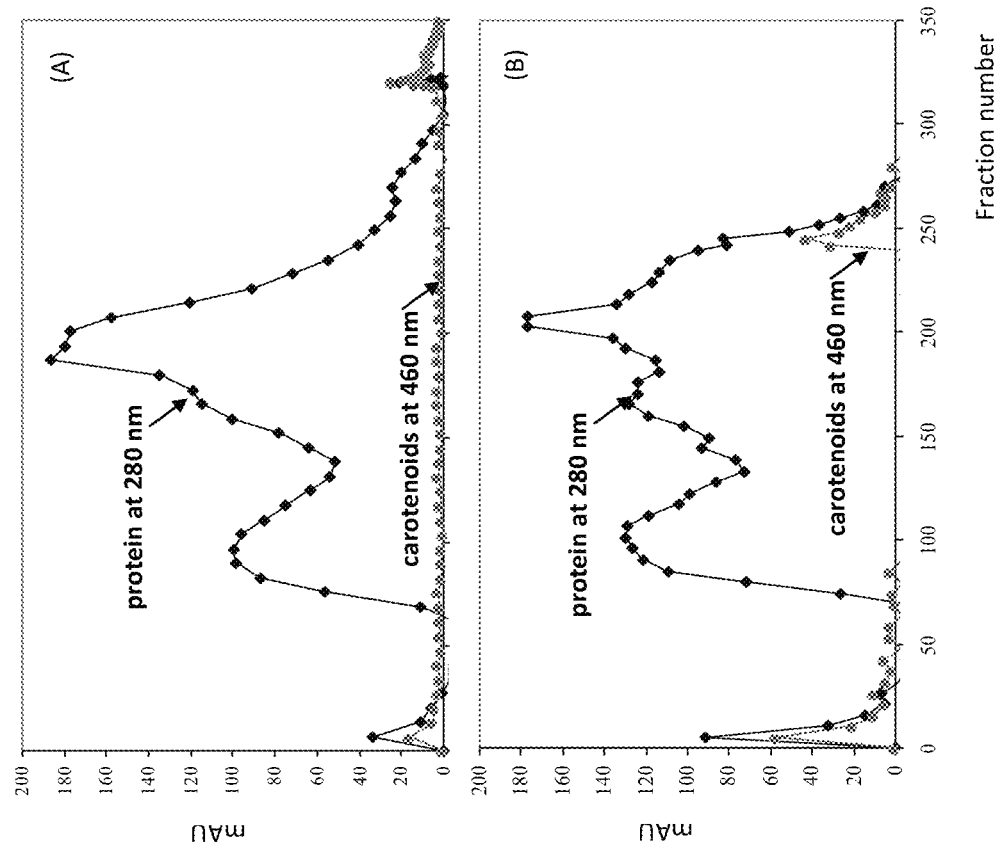
FIG. 8 shows elution profile of the lutein-binding protein on gel filtration where the pigmented-sericin solution obtained from degumming process at 121° C. for 15 (A) and 30 (B) min were loaded onto a Sephacryl S-200 column and eluted with 20 mM Tris-HCl buffer, pH 7.0. Fractions were monitored for protein at 280 nm, carotenoids at 460 nm.

Reference will now be made in detail to an exemplary embodiment of the present invention, examples of which are illustrated in the accompanying drawings. While the invention will be described in conjunction with the embodiment, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention For purposes of brevity and clarity, descriptions of embodiments of the present invention are limited hereinafter to a lutein extraction method 100. This however does not preclude embodiments of the invention where fundamental principals prevalent among the various embodiments of the invention such as operational, functional or performance characteristics are required.

An exemplary embodiment of the invention, a lutein extraction method 100 from silk fibers, is described hereinafter with reference to FIGS. 1 to 8. The lutein extraction method 100 is also referred to hereinafter as a method for obtaining silk extract containing lutein. The source of the silk fibers is preferably silk cocoons due to its natural selecting ability for lutein. The lutein extraction method is achieved with solvents that are not harmful. The solvents used can even be recycled for further lutein extraction. Preferably, the method for lutein extraction is conducted at neutral pH and at ambient temperature and pressure. However, lutein extraction according to the method can be achieved at high temperature and pressure without changes to the lutein isomer when shorter lutein production time is required. Lutein-binding protein from silk has higher bioactivity and bioavailability than commercial lutein ester in both cell culture and animal models. Prevention of lipid peroxidation of lutein from silk is found to be five times more effective than lutein ester in retina cells Immunity of mice fed lutein from silk is also twice as high as those fed with lutein ester. Lutein extracted from silk fibers is therefore very suitable for food supplement and pharmaceutical products.

In the lutein extraction method 100, yellow silk cocoons are first degummed to partially remove glutinous silk protein sericin in a step 110. The pieces of yellow silk cocoons were then soaked in distilled water with a ratio of 1:30 prior to being heated at 121° C. for 15 mins. After being heated, degummed cocoons and degumming solution, called pigmented-sericin solution, were separated off, leaving degummed cocoons. The degummed cocoons are also known as silk fibers. Besides silk cocoon, silk yarn and silk waste can be used as a replacement for the silk cocoon to obtain silk fibers therefrom.

Next, the degummed cocoons were contacted with extraction solvents in a step 120 to obtain a first solution therefrom. Specifically, the degummed cocoons of the step 110, with 3 g of initial weight, were placed in a container, preferably a 250 mL Erlenmeyer flask, and mixed with 90 mL the extraction solvents as described above. Preferably, the extraction solvent comprises one or more of hexane, ethyl alcohol and ethyl acetate. Further, it is preferred that the extraction solvent contains 0.1% (w/v) of Butylated Hydroxytoluene (BHT) and 0.1% (w/v) of Butylated Hydroxyanisole (BHA).

The mixture was shaken in a shaker at 140 rpm/min for 2 hours under dim light at room temperature. An organic solution was collected therefrom and kept in an amber glass sample bottle at 4° C. The degummed cocoons were repeatedly contacted with the extraction solvent three times under the same condition to obtain multiple organic solution portions. The multiple organic solution portions were pooled together to obtain the first solution.

The first solution was then partitioned into non-aqueous phase and an aqueous phase in a step 130. In the step 130, 100 mL of aqueous sodium chloride (NaCl) at 10% (w/v) was added to the first solution to extract the non-aqueous phase therefrom. The supernatant was then separated from the non-aqueous phase before being subjected to further extraction of non-aqueous phase therefrom. The extraction of the non-aqueous phase was repeated until the supernatant portion became substantially colourless with the aqueous phase being the remaining colourless supernatant portion.

Next, the non-aqueous phase is then concentrated, via water and/or polar substance removal, or dried in a step 140 to obtain dried residue therefrom. Drying of the non-aqueous phase is achieved by adding anhydrous sodium sulfate, preferably 2 g thereof, to the non-aqueous phase. Alternatively or in addition to the anhydrous sodium sulfate, one or a combination of di-sodium phosphate, tri-sodium phosphate, sodium citrate and solutions containing sodium ions may be used for drying the non-aqueous phase. Additionally, the non-aqueous phase is further dried via vacuum evaporation at 35° C. to obtain the dried residue.

In a step 150, the dried residue is dissolved in the one or more solvents to obtain a second solution therefrom. Preferably, the dried residue is dissolved in hexane/ethyl acetate (3:1, v/v) to obtain a preferred volume of 5 to 10 mL, depending on the carotenoid content. The second solution is then filtered through a 0.45 μm PTFE syringe filter in a step 160 to obtain lutein extract therefrom. The lutein extract is then kept under nitrogen gas in the dark at −20° C. until further analysis.

To assess the extraction efficiency of the lutein extraction method 100, the total carotenoids and lutein extracted using the extraction solvents of hexane, ethanol and ethyl acetate (3:2:1, v/v/v) were compared with those extracted under other solvent systems including (S1) hexane/ethanol (3:4, v/v), (S2) hexane/acetone (5:3, v/v), (S3) hexane/acetone/ethanol (3:1:2, v/v/v), (S4) hexane/ethyl acetate (1:1, v/v), (S5) ethyl acetate (100%); and (S6) hexane (100%). For the extract solutions in acetone based extracting solvents (S2 and S3), a 100 mL of distilled water was added in order to remove acetone. The extraction efficiency of the extracting solvents was compared by means of spectrophotometrical quantification of the amount of total carotenoids and lutein content. The UV/VIS absorption spectra of the pigment extracts was determined as first criteria of identification and characterization of the carotenoid compositions.

Two specific exemplary applications of the lutein extraction method 100 are described hereinafter.

Example 1

In a first exemplary application of the lutein extraction method 100, a sample (1±0.0002 g) of silk cocoons was degummed with 30 mL of distilled water at 121° C. for 15 min. The degummed cocoons (P1) were fourfold extracted with 30 mL of hexane, ethanol and ethyl acetate (3:2:1, v/v/v) with 0.1% BHT (w/v) until it became colorless. For the pigmented-sericin solution (P2), the extraction was done in an amber glass separating funnel by using 60 mL of the same extracting solvent before being partitioned to obtain an upper phase. The upper phase was then evaporated to dryness under vacuum, leaving dried residues. The dried residues were dissolved in HPLC grade n-hexane/ethyl acetate (3:1, v/v) and adjusted to a final volume of 5 mL before being filtered through a 0.45 μm filter membrane. The filtered solution was then kept under nitrogen gas at −20° C. for subsequent analysis. Carotenoids extracted from the degummed cocoons and the pigmented-sericin solutions were identified by high performance liquid chromatography (HPLC). The absorption spectra and the concentration of carotenoids and lutein in the pigment extracts were determined in ethanol using spectrophotometer.

Example 2

In a second exemplary application of the lutein extraction method 100, pigmented-sericin complexes were isolated from yellow silk cocoons via five different treatments. The five different treatments comprise degumming the yellow silk cocoons at 121° C. for durations of 15, 30, 60, 90, and 120 min. For each of the treatments, yellow silk cocoons were degummed with deionized water in a ratio of 1:30 under dark. After the elapse of the respective duration for treatment, the mixtures were cooled to room temperature and the degumming solutions were separated off. Deionized water was used for adjusting to a 100-mL final volume of each pigmented-sericin solution derived from the different treatments. All treatments were done in triplicate. The total level of protein in the pigmented-sericin solutions was determined using bicinchoninic acid (BCA) protein assay kit. The assay was carried out at 37° C. for 30 min with bovine serum albumin (BSA) as a standard.

Further purification and concentration were carried out by ammonium sulfate precipitation with minimum illumination. Solid ammonium sulfate was added slowly to each pigmented-sericin solution, while being continuously stirred, to achieve 45% saturation. The suspension was maintained in an ice bath for 30 min before centrifugation at 10,000×g at 4° C. for 30 min. The obtained pellet was discarded before remaining suspension was buffered in 20 mM of Tris-HCl containing 150 mM of NaCl at pH 7.0. The concentrated solution of pigmented-sericin complexes was filtered through a 0.45 μm regenerated cellulose syringe filter membrane.

For the characterization of lutein in protein-binding form or sericin-lutein complex, a modified form of anion exchange chromatography was utilised. Fractionation was performed under AKTA explorer system. An aqueous pigmented-sericin solution, obtained from each of the five treatments, was filtered through a 0.45 μm syringe filter membrane. A protein sample was loaded on a weak anion exchange DEAE Hi-Trap 1-ml column, pre-equilibrated with 10 mM of BisTris-HCl at pH 7.0. The fractions were eluted using a 1 M NaCl linear gradient in the same buffer for collecting 5 mL fractions. All fractions were monitored for peptides, protein and lutein at 254, 280 and 460 nm. In order to optimize the separation, a strong anion exchange QXL-1 ml column was used for comparison.

The concentrated samples of the pigmented-sericin solutions in 20 mM of Tris-HCl buffer at pH 7.0 containing 150 mM of NaCl was characterized according to molecular size. The sample was loaded onto a Sephacryl S-200 column (1.6 cm×80 cm) pre-equilibrated with 20 mM of Tris-HCl buffer at pH 7.0 containing 150 mM of NaCl. Elution was performed with the same buffer at a flow rate of 0.5 mL min$^{-1}$ under AKTA explorer system as described earlier. All fractions were monitored for peptides, protein and lutein at 254, 280 and 460 nm, respectively for collecting 0.5-mL fractions. The elution profile of the samples was evaluated.

High Temperature Extraction

Figure 9A:
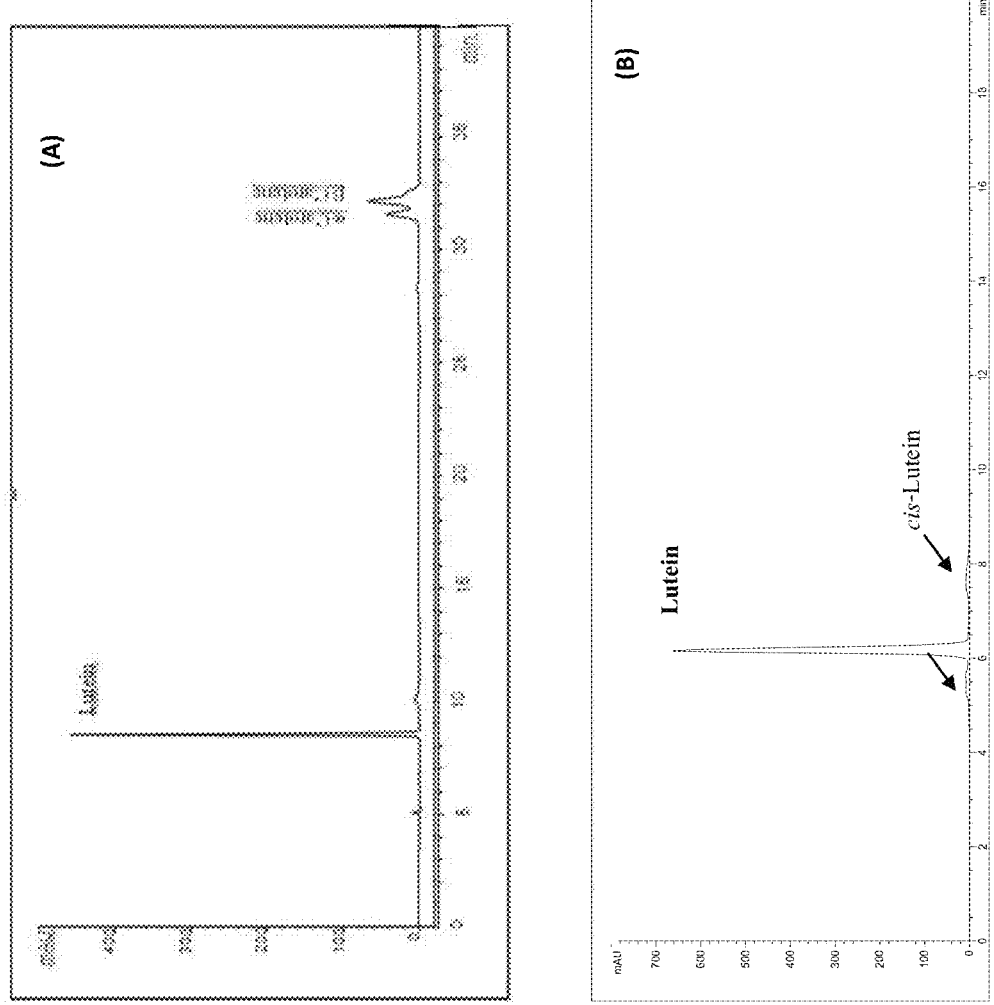
FIGS. 9a to 9c show chromatograms of lutein standard (A), lutein extracted by organic solvent (B), lutein extracted by a speed extractor by using pressure=100 bar, temperature of 35 C for 10 minutes (C), temperature of 35 C for 20 minutes (D), temperature of 50 C for 10 minutes (E), and temperature of 100 C for 10 minutes (F). Results were analyzed by C18 RP-HPLC, using acetronitrile/methanol (9:1, v/v) and ethyl acetate as a mobile phase.
Figure 9B:
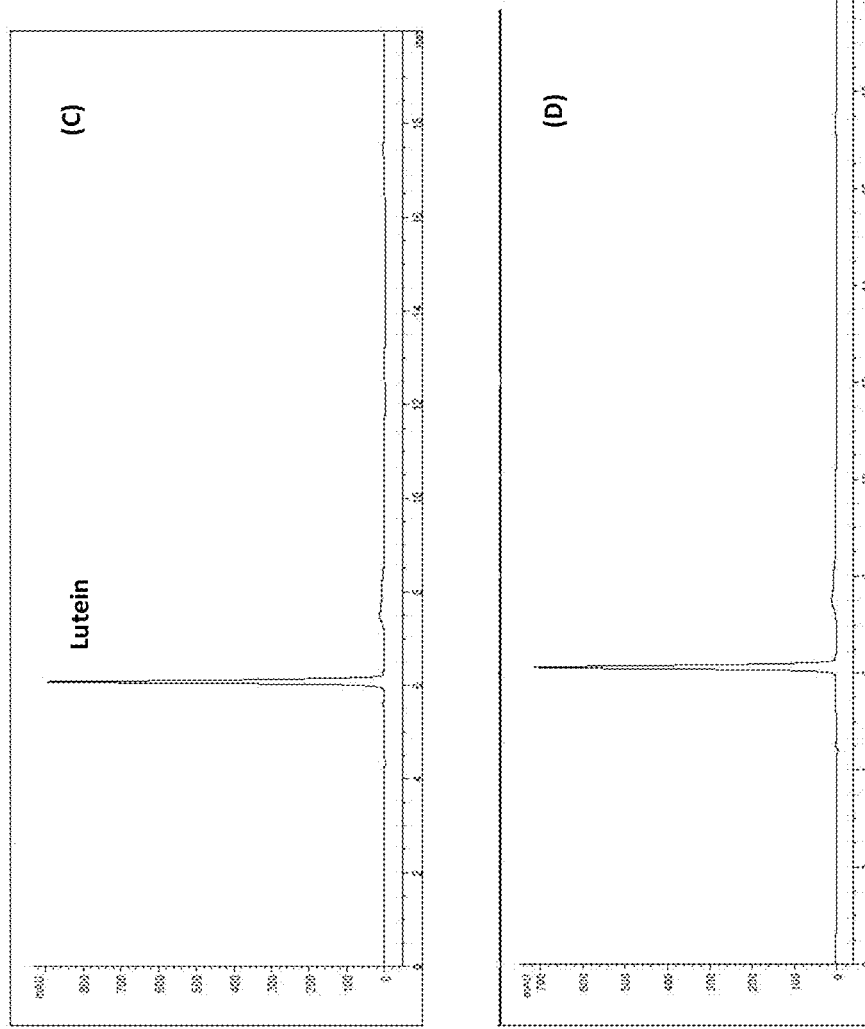
Figure 9C:
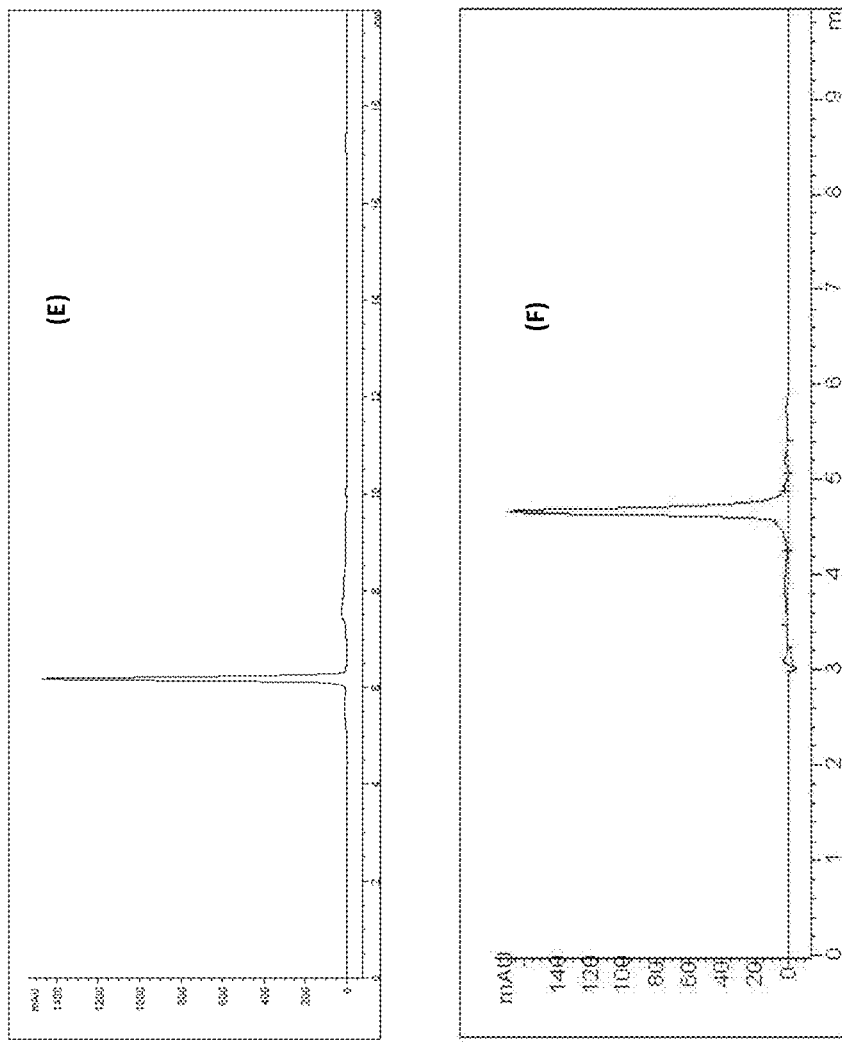

Lutein was extracted at high temperature at various time durations using the lutein extraction method 100. FIGS. 9a to 9c show chromatograms of lutein extracted by organic solvent (A), lutein extracted by a speed extractor machine at a pressure of 100 bar and 100 Celcius for 10 minutes (B), at 100 Celcius for 30 minutes (C), at 150 Celcius for 10 minutes (D). Chromatogram results were analysed by C18RP-HPLC and using acetronitrile/methanol (9:1, volume/volume) and ethyle acetate as a mobile phase. It is observed that extraction of lutein at high temperature and high pressure (using the solvents of the lutein extraction method 100) shows that high temperature and pressure does not compromise or damage the extracted lutein.

Effects of Lutein to Lipid Peroxidation in Retinal Pigment Epithelial Cells.

Figure 10:
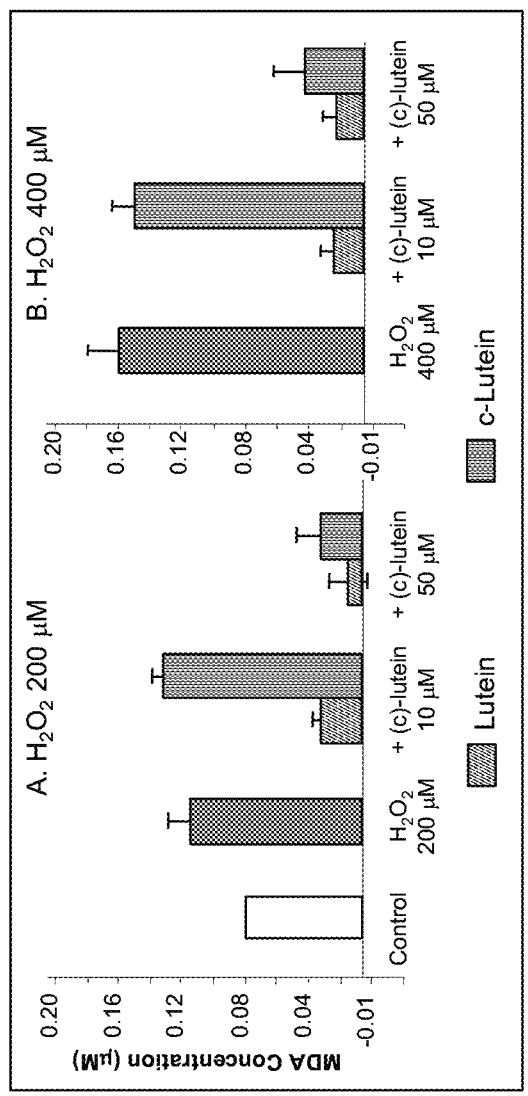
FIG. 10 shows the effect of lutein to lipid peroxidation in retinal pigment epithelial cell (ARPE-19) with lutein from cocoon (lutein) and lutein from marigold flower (c-lutein) at concentrations of 1, 10 and 50 µM for 2 hrs before adding of 200 µM (A) or 400 µM (B) of $H_2O_2$ with lipid peroxidation being measured after 24 hours by TBARs assay (result is shown in amount of MDA with the graphs indicating Mean±SEM from 3 experiments which duplicate tests for each experiment)

Effects of lutein obtained from the lutein extraction method were tested on human retinal pigment epithelial (RPE) cell culture. The RPE cell line, ARPE-19 (American Type Culture Collection, ATCC) was cultured in cell media DMEM/F-12 with 10% fetal bovine serum (FBS) and penicillin/streptomycin in 5% $CO_2$ cell incubator at 37° C. (change of cell media every 3-4 days with subculture by trypsin/EDTA solution). The results are shown in FIG. 10.

Oxidative stress condition was induced in the cell culture under two separate treatments. For a first treatment, a first RPE cell culture portion was treated by $H_2O_2$ after 4 hours with results assessed after 24 hours. For a second treatment, a second RPE cell culture portion was treated by $H_2O_2$ after 2 hrs with results assessed after 12 and 24 hrs.

For the first treatment, ARPE-19 and HLE-B3 cells were cultured in a 96 well-plate (20,000 cells/well) in DMEM/F-12 cell medium as above said method. When cells are 24 hours of age, cell medium was changed to serum free medium. Then, induce oxidative stress condition in cells by adding 50-800 μM $H_2O_2$ solution (or higher concentrate in some experiment) before incubation in a cell incubator of 5% $CO_2$ at 37° C. for 4 and 24 hours before subsequent testing of cell viability.

For the second treatment, ARPE-19 cells were cultured in a 96 well-plate in 10% FBS-DMEM/F12 cell medium and for lens HLE-B3 cell in 20% FBS-DMEM/F12 cell medium for 24 hours before changing the cell medium to serum free DMEM/F12 cell medium. 25-1600 μM of $H_2O_2$ solution was then added prior to incubation at 37° C. in 5% $CO_2$ for 2 hours. The cell medium was then changed to serum free DMEM/F12 cell medium before incubation at 37° C. in 5% $CO_2$ for 12 and 24 hours. Cells were subsequently tested for cell viability.

For a third treatment, retinal epithelial cells ARPE-19 were cultured in 96 black well plate in DMEM/F12 medium with 10% FBS. Lens HLE-B3 cells were cultured in 20% FBS DMEM/F12 for 24 hrs before changing the cell medium to serum free DMEM/F12 without phenol red and before bringing the cells under UV-B 50 μl. The cells were subjected to UV irradiation in a UV irradiation chamber using a radiation dose of UV-B at 20-500 mJ/cm$^2$. The cell medium was then changed to serum free DMEM/F12 before the cells were cultured in an incubator at 5% $CO_2$ at 37° C. for 12 and 24 hrs. The cells were subsequently tested for cell viability.

Amount of cell viability for the various treatments were checked using an MTT assay method [3-(3,5-dimethylthiazol-2,5-diphenyltetra-zolium bromide)]. 2 hours before the various treatments, MTT solution (5 mg/ml PBS) was added into the cell medium until the last concentration is 0.5 mg/ml. The cell medium was subsequently removed before 200 μl DMSO:ethanol (1:1) was added for dissolving formazan crytal. Absorbance was then checked by an ELISA reader at 595 nm.

Lipid peroxidation reaction was measured by thiobarbituric acid reactive substance (TBARs assay) after oxidative stress condition were induced in cells by H2O2 or UV. TBARs reagent (10% trichloroacetic acid, 1% thiobarbituric acid, 5% HCl and 1% SDS) were then added for incubation at 90° C. for 1 hour before being cooled and centrifuged at 5000 rpm for 5 minute. The fluorescence value of the supernatant was then measured at Ex 535 nm and Em 595 nm.

Study of Lutein Effects Using Laboratory Animals

Mice were used to study the effects of lutein extracted from yellow silk cocoon using the lutein extraction method 100 against other sources of lutein. Mice is a laboratory animal typically used in the study of immunomodulatory effect of a group of carotenoids. Female BALB/c mice 7 weeks of age from National Laboratory Animal Center of Mahidol University were used for this study at the Laboratory Animal Center of Faculty of Medical Science Naresuan University in a light-ing controlled room at 12:12 hours of light-dark cycle hours at 25±1° C. The mice were fed with sterilized distilled water for this study.

The mice were divided into five groups where:
Group 1 was only fed solvent for lutein (1% Tween 80 in PBS pH 7.4; vehicle control);
Group 2 was fed lutein extracted from yellow cocoon at 10 mg/kg body weight (sLT10);
Group 3 was fed with lutein extracted from yellow cocoon at 20 mg/kg body weight (sLT20);
Group 4 was fed with commercial lutein extracted from marigold flower (xanthophylls≥95%; P.R. China) at 10 mg/kg body weight (cLT10); and
Group 5 was fed with commercial lutein extracted from marigold flower (xanthophylls≥95%; P.R. China) at 20 mg/kg body weight (cLT20).

All 5 groups of mice took lutein or solvent (oral administration) at volume 200 ul/a mouse everyday (between 7.30 am to 8.30 am) for 12 weeks. The weight of each mouse was recorded before the start of the experiment and once every week until the completion of the experiment.

Five mice were selected from each of Groups 1 to 5 in weeks 2, 4, 8 and 12 after being fed lutein or solvent to study time response of immunologic activity. The selected mice were mercy-killed by providing an overdose of pentobarbital sodium intra-peritoneally. The thorax and abdomen of the mice were opened for collecting blood from the heart and other organs including the thymus, spleen, liver, kidney and lung. The weight of the organs of each of the mice in each group was recorded while the blood and spleen of each mice were studied for immunologic activity.

When testing lymphocyte activity from the mice that took lutein and were activated by mitogen (LPS type at 2.5 and 5 ug/ml), it was found that the lymphocyte from the mice that took lutein from yellow cocoon at 10 and 20 mg/kg BW/day for 4 weeks has better proliferation ability than lymphocyte from the mice that did not take lutein. When lutein from marigold flower was fed to mice at only at 20 mg/kg BW/day, lymphocyte was proliferated as shown in FIG. 11. FIG. 11 shows that lutein from yellow cocoon at both 10 and 20 mg/kg BW/day and lutein from marigold flower at 20 mg/kg BW/day when fed to mice for 4 weeks have effects to the activity of B lymphocyte ability. It is noted that when the dose of lutein from yellow cocoon fed to the mice was only 10 mg/kg BW/day, it has the same effect on proliferation ability of B lymphocyte as mice being fed lutein from marigold flower in higher dose (20 mg/kg BW/day). The test results for lymphocyte activity activated by mitogen of PWM type were the same as the results for LPS type. The lutein from yellow cocoon at 10 and 20 mg/kg BW/day is able to generate more lymphocyte activity. However, lutein from marigold flower in any dose, when fed to mice at 10 and 20 mg/kg BW/day, has no effect on lymphocyte activity.

In a forgoing manner, a method for lutein extraction is described according to an exemplary embodiment of the invention. Although only one embodiment of the invention is disclosed in this document, it will be apparent to one skilled in the art in view of this disclosure that numerous changes and/or modifications can be made to the disclosed embodiment without departing from the scope and spirit of the invention.

The invention claimed is:
1. A method for lutein extraction comprising:
  contacting silk fibres with a plurality of solvents to obtain a first solution, wherein the plurality of solvents comprise hexane, ethyl alcohol and ethyl acetate;
  partitioning the first solution into non-aqueous phase and an aqueous phase;
  drying the non-aqueous phase to obtain dried residue;
  dissolving the dried residue with one or more of the plurality of solvents to obtain a second solution; and
  filtering the second solution to obtain lutein extract therefrom.
2. The method as in claim 1, further comprising:
  degumming at least one of silk cocoon, silk yarn and silk waste to obtain the silk fibres.
3. The method as in laim 2, wherein degumming at least one of silk cocoon, silk yarn and silk waste comprises:
  soaking the at least one of silk cocoon, silk yarn and silk waste in water to obtain degumming solution; and
  removing the degumming solution to obtain the silk fibres.
4. The method as in claim 3, wherein degumming at least one of silk cocoon, silk yarn and silk waste comprises:
  heating the water-soaked at least one or silk cocoon, silk yarn and silk waste.
5. The method as in claim 1, wherein contacting silk fibres with the plurality of solvents comprises:
  extracting a plurality of organic solution portions from the silk fibres by contacting the silk fibres with the plurality of solvents; and
  pooling the plurality of organic solutions to obtain the first solution.
6. The method as in claim 1, wherein partitioning the first solution comprises:
  adding aqueous sodium chloride to the first solution.
7. The method as in claim 1, wherein drying the non-aqueous phase comprises:
  separating the aqueous phase from the non-aqueous phase; and
  adding anhydrous sodium sulfate to the separated non-aqueous phase.
8. The method as in claim 7, wherein drying the non-aqueous phase further comprises:
  evaporating the separate non-aqueous phase to dryness.
9. The method as in claim 1, wherein dissolving the dried residue comprises:
  dissolving the dried residue in hexane and ethyl acetate.
10. The method as in claim 1, herein the filtering step comprises filtering the second solution through a syringe filter.
11. A method for lutein extraction comprising:
  degumming the silk cocoon to obtain silk fibres;
  contacting the silk fibres with one or more solvents to obtain an first solution, wherein the one or more solvents comprises hexane, ethyl alcohol and ethyl acetate;
  partitioning the first solution into non-aqueous phase and an aqueous phase;
  drying the non-aqueous phase to obtain dried residue;
  dissolving the dried residue with hexane and ethyl acetate to obtain a second solution; and
  filtering the second solution to obtain lutein extract therefrom.
12. The method as in claim 11, wherein partitioning the first solution comprises:
  adding aqueous sodium chloride to the first solution.
13. The method as in claim 11, wherein drying the non-aqueous phase comprises:
  separating the aqueous phase from the non-aqueous phase; and
  adding anhydrous sodium sulfate to the separated non-aqueous phase.
14. The method as in claim 13, wherein drying the non-aqueous phase further comprises:
  evaporating the separated non-aqueous phase to dryness.
15. The method as in claim 11, wherein dissolving the dried residue comprises:
  dissolving the dried residue in hexane and ethyl acetate.

16. The method as in claim 11, wherein the filtering step comprises filtering the second solution through a syringe filter.

17. A method for lutein extraction comprising:
contacting silk fibres with one or more solvents to obtain a first solution, wherein the one or more solvents comprises hexane, ethyl alcohol and ethyl acetate;
partitioning the first solution into non-aqueous phase and an aqueous phase;
drying the non-aqueous phase to obtain dried residue;
dissolving the dried residue with the one or more solvents to obtain a second solution; and
filtering the second solution to obtain lutein extract therefrom.

* * * * *